United States Patent [19]

Hafler et al.

[11] Patent Number: 5,571,499

[45] Date of Patent: *Nov. 5, 1996

[54] TREATMENT OF AUTOIMMUNE DISEASES BY AEROSOL ADMINISTRATION OF AUTOANTIGENS

[75] Inventors: David A. Hafler, W. Newton; Howard L. Weiner, Brookline, both of Mass.

[73] Assignee: Autoimmune, Inc., Lexington, Mass.

[*] Notice: The term of this patent shall not extend beyond the expiration date of Pat. No. 5,571,500.

[21] Appl. No.: 465,815

[22] Filed: Jun. 6, 1995

Related U.S. Application Data

[63] Continuation of Ser. No. 419,502, Apr. 10, 1995, which is a continuation of Ser. No. 53,306, Apr. 26, 1993, abandoned, which is a continuation of Ser. No. 454,806, Dec. 20, 1989, abandoned, which is a continuation-in-part of Ser. No. 379,778, Jul. 14, 1989, abandoned, which is a continuation-in-part of Ser. No. 2,139, which is a continuation-in-part of Ser. No. 65,734, Jun. 24, 1987, abandoned.

[51] Int. Cl.$^6$ .............................. A61K 9/12; A61K 38/02
[52] U.S. Cl. .............................. 414/43; 424/44; 424/45; 424/46; 514/2; 514/825; 514/903
[58] Field of Search .............................. 424/43–45, 46; 514/2, 825, 903

[56] References Cited

U.S. PATENT DOCUMENTS

| | | | |
|---|---|---|---|
| 3,739,951 | 6/1973 | Geller et al. | 222/630 |
| 4,352,789 | 10/1982 | Thiel et al. | 424/46 |
| 4,548,922 | 10/1985 | Carey et al. | 514/4 |
| 4,681,760 | 7/1987 | Fathman et al. | 424/154.1 |
| 4,789,660 | 12/1988 | Enever et al. | 514/4 |

FOREIGN PATENT DOCUMENTS

| | | |
|---|---|---|
| 0272097 | 6/1988 | European Pat. Off. . |
| 88/10120 | 12/1988 | WIPO . |
| 88/02139 | 12/1988 | WIPO . |
| 92/06704 | 4/1992 | WIPO . |
| 92/07581 | 5/1992 | WIPO . |
| 93/16724 | 9/1993 | WIPO . |

OTHER PUBLICATIONS

Newman S. P., in., Aerosols and the Lung, Clarke, S. W. and Davis, D. eds. Butterworth, London, England, (1984).
Holt, P. G. et al., Immunology Today, 8:14–16, (1987).
Sedgwick, J. D. et al., Eur. J. Immuno., 14:893–897, (1984).
Laube et al., JAMA, 269(16):2106 (1993).
Dean et al., Diabetologia, 29:339 (1986).
Barr, M., Practical Pharmacy Edition, 19(11):675 (1958).
Whitacre, C. C. et al. (Abstract), Sixth International Congress Immunology, Toronto, Canada, Jul. 7–11, 1986.
Thompson, H. S. G. et al., Clin. Exp. Immunol. 6: 581–586, (1986).
Bitar, D. et al., Cell Immunol. 112: 364–370, (1988).
Higgins, P. J. and Weiner, H. L., Annals of Neurology 20(1):162(1986) (Abstract).
Higgins, P. J. and Weiner, H. L., J. Neuroimmunol. 16: 77 (Abstract) (1987).
Higgins, P. J. and Weiner, H. L., J. Immunol. 140: 440–445, (1988).
Lider, O., et al., J. Immunol. 142: 748–752, (1989).
Traugott et al., J. of the Neuro. Sci., 56:65 (1982).
Raine et al., Lab. Invest., 48:275 (1983).
Nagler–Anderson et al., Proc. Nat. Acad. Sci. USA, 83:7443 (1986).
Braley–Mullen et al., Cell. Immunol., 51:408 (1980).
McKenna et al., Cell. Immunol., 81:391 (1983).
Belik et al., Vopr. Med. Khim., 24:377 (1978).
Sriram et al., Cell. Immunol., 75:378 (1983).

(List continued on next page.)

*Primary Examiner*—Gollamudi S. Kishore
*Attorney, Agent, or Firm*—Darby & Darby, P.C.

[57] ABSTRACT

Disclosed herein is a method for treating autoimmune diseases in mammals by administration of one or more agents selected from the group consisting of autoantigens specific for the autoimmune disease, disease-suppressive fragments and analogs of said autoantigen in aerosol form.

14 Claims, 6 Drawing Sheets

OTHER PUBLICATIONS

Lando et al., J. Immunol., 126:1526 (1981).
Hubbard et al., Proc. Natl. Acad. Sci. USA, 86:680 (1989).
Holt et al., Immunol., 42:409 (1981).
Sedgewick et al., Immunol., 56:635 (1985).
Holt et al., Immunol., 60:97 (1987).
Sedgewick et al., Cell. Immunol., 94:182 (1985).
Hara et al., J. Immunol., 48(6):1685 (1992).
Wood et al., Transplantation, 39(1):56 (1985).
Zhang et al., Proc. Natl. Acad. Sci. USA, 88:10252 (1991).

SCORES vs PI

- CONTROL (□)
- MBP—0.005mg ORAL (●)
- MBP—0.005mg AEROSOL (○)

FIG. 3B

SCORES vs PI

- CONTROL (●)
- FED 0.05mg (○)
- AEROSOL 0.05mg (□)

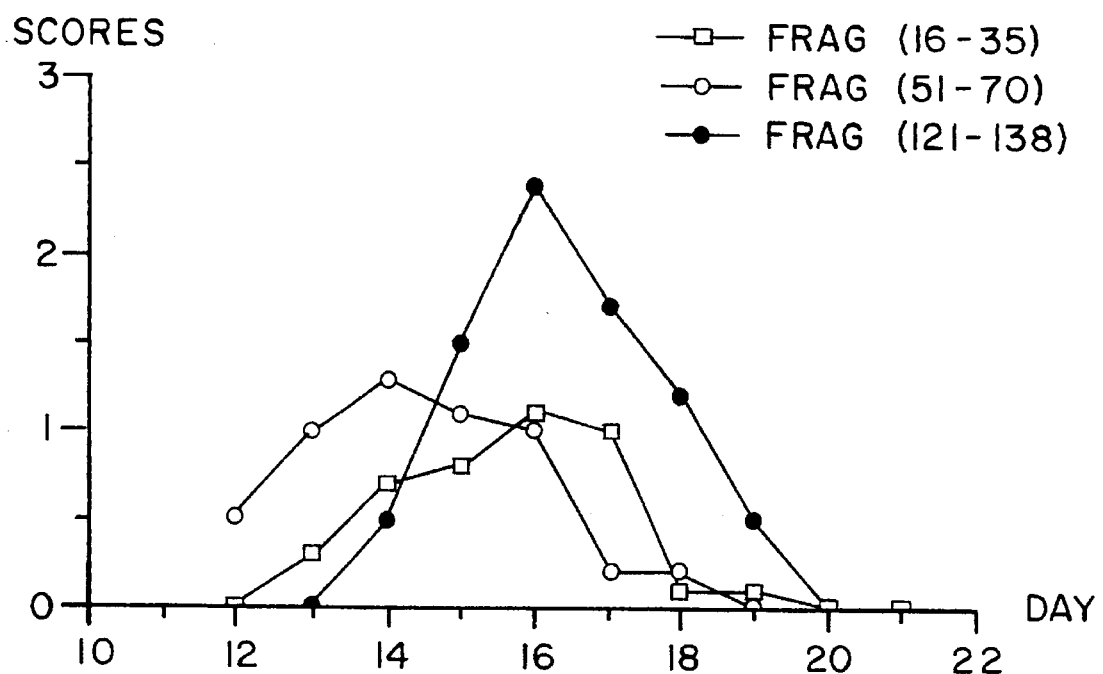
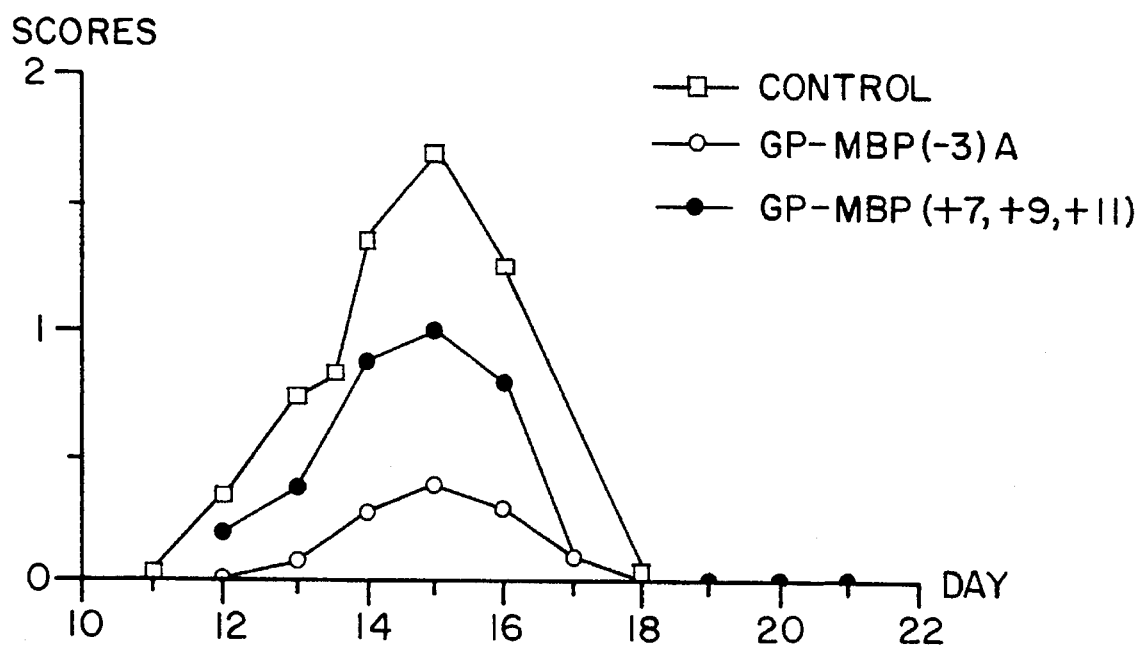

TREATMENT OF AUTOIMMUNE DISEASES BY AEROSOL ADMINISTRATION OF AUTOANTIGENS

This is a continuation of application Ser. No. 08/419,502, filed Apr. 10, 1995, now abandoned; which is a continuation of application Ser. No. 08/053,306, filed Apr. 26, 1993, now abandoned; which is a continuation of application Ser. No. 07/454,806, filed Dec. 20, 1989, now abandoned; which is a continuation-in-part of application Ser. No. 07/379,778 filed Jul. 14, 1989, now abandoned; which is a continuation-in-part of application Ser. No. 01/002,139, filed Jun. 24, 1988, (International application No. PCT/US88/02139), now abandoned; which is a continuation-in-part of application Ser. No. 07/065,734, filed Jun. 24, 1987.

BACKGROUND OF THE INVENTION

This invention pertains to an improvement in the treatment of autoimmune diseases. More specifically, the invention is directed to the administration of autoantigens and biologically active fragments or analogs of such autoantigens in aerosol form for the prevention and therapeutic treatment of autoimmune diseases. The invention also includes aerosol formulations of autoantigens useful in the treatment of autoimmune diseases in mammals.

Autoimmune diseases are characterized by an abnormal immune response involving either cells or antibodies, that are in either case directed against normal autologous tissues.

Autoimmune diseases in mammals can generally be classified in one of two different categories: cell-mediated disease (i.e. T-cell) or antibody-mediated disorders. Non-limiting examples of cell-mediated autoimmune diseases include multiple sclerosis, rheumatoid arthritis, autoimmune thyroiditis, diabetes mellitus (Juvenile onset diabetes) and autoimmune uveoretinitis. Antibody-mediated autoimmune disorders include myasthenia gravis and systemic lupus erythematosus (or SLE).

The current treatments for both categories of autoimmune diseases involve administration of drugs which non-specifically suppress the immune response. Examples of such drugs are methotrexate, cyclophosphamide, Imuran (azathioprine) and cyclosporin A. Steroid compounds such as prednisone and methylprednisilone are also employed in many instances. These drugs have limited efficacy against both cell- and antibody- mediated autoimmune diseases. Use of such drugs is limited by virtue of their toxic side effects and also because they induce "global" immunosuppression in a patient receiving prolonged treatment with the drug, e.g. the normal protective immune response to pathogenic microorganisms is downregulated thereby increasing the risk of infections caused by these pathogens. A further drawback is that there is an increased risk that malignancies will develop in patients receiving prolonged global immunosuppression.

Other therapies have been proposed for the treatment of autoimmune diseases. U.S. patent application Ser. No. 65,794 filed Jun. 24, 1987 (now abandoned) and copending International Patent Application PCT/US88/02139 filed Jun. 24, 1988, disclose that the oral or enteral administration of relatively high levels of myelin basic protein (MBP) and disease-inducing and non-inducing fragments and analogs thereof is effective in suppressing acute monophasic experimental allergic encephalomyelitis (EAE), an induced T-cell-mediated autoimmune disease directed against myelin basic protein. EAE is a recognized and widely used animal model for multiple sclerosis (MS). The above-identified applications also disclose that the oral or enteral administration of *Mycobacterium tuberculosis* is an effective treatment for suppressing adjuvant arthritis and extrapolate the aforementioned results to the treatment of other autoimmune diseases.

Copending U.S. patent application Ser. No. 379,778 filed Jul. 14, 1989 discloses the oral or enteral administration of S-antigen for the treatment of autoimmune uveoretinitis.

Various methods have been employed to induce antigen-specific suppression of EAE such as immunization with MBP emulsified in incomplete Freund's adjuvant (Lando, Z. et al., *J. P. Immunol.*, 126: 1526, 1981), or an intravenous injection of MBP coupled to lymphoid cells (Sriram, et al., *Cell Immunol.* 75: 378, 1983).

Traugott et al., *J. Neurol. Sci.* 56: 65–73, 1982 and Raine et al., *Lab. Investigation* 48: 275–84, 1983 teach that treatment of a strain of guinea pigs suffering from chronic relapsing EAE by parenteral administration of MBP alone or, in incomplete Freund's adjuvant (IFA) or, in combination with galactocerebroside, a lipid hapten of myelin, suppressed the clinical symptoms of EAE.

Based on an English language abstract, Belik et al., *Vopr. Mev. Khin.* 24: 372–377, 1978, disclose the parenteral administration of "alkaline myelin protein fragment (AMPF)" and "synthetic encephalitogenic peptide (SEP)" to guinea pigs with EAE. The animals had been sensitized by bovine AMPF or synthetic SEP but recovered after administration of AMPF.

Braley-Mullen et al., *Cell Immun.* 51: 408, 1980, disclose the suppression of the symptoms of experimental autoimmune thyroiditis in guinea pigs by injection of thyroglobulin antigen in IFA.

Nagler-Anderson et al., *Proc. Natl. Sci. USA* 83: 7443–7446, 1986 disclose the oral administration of collagen to suppress collagen-induced arthritis in a mouse model. Type II collagen-induced arthritis was suppressed in the mouse by intragastric administration of soluble, but not denatured, Type II collagen prior to immunization of the animal with Type II collagen in an adjuvant. The Nagler-Anderson antigen was not administered in aerosol form.

Other investigators have examined the effects of aerosolized proteins on the treatment of genetic diseases and on modulating the IgE response in mammals.

Hubbard, R. C. et al. (*Proc. Natl. Acad. Sci.* (USA) 86: 680–684, 1989) demonstrated the feasibility of administered proteins to mammals in aerosol form. Hubbard et al. disclose administration of a relatively large protein alpha$_1$-antitrypsin (AAt) via the pulmonary epithelial surface for the treatment of alpha anti-trypsin deficiency, an inherited genetic disease. AAt, a 45,000 dalton molecular weight single-chain polypeptide (that functions as an inhibitor of neutrophil elastase) was administered to sheep in an aerosol form. Aerosolized AAt remained fully functional and intact in the tissues of the mammal to which the material was administered and diffused across the alveolar epithelium, as evidenced by the presence of AAt in the lung, lymph and blood tissue.

Holt, P. G. et al., *Immunol.* 42: 409–417, 1981 disclose the inhibition of specific IgE responses in mice by pre-exposure to inhaled antigens. The exposure of mice to aerosolized ovalbumin once weekly for seven weeks caused the suppression of IgE responses when these animals were challenged intraperitoneally with soluble or alum-precipitated ovalbumin.

Sedgwick, J. D. et al., *Immunol.* 56: 635–642, 1985 reported on the down-regulation of the specific IgE response to an inhaled antigen. Repeated exposure of rats to an aerosol of ovalbumin induced carrier-specific tolerance to subsequent challenge with the same antigen.

Holt, E. G. et al., *Immunol.* 60: 97–102, 1987 disclose that repeated inhalation of low levels of ovalbumin by mice or rats preferentially induced tolerance to the IgE antibody class and postulated that this process represented an important protective mechanism that normally prevents allergic sensitization of a mammal to air-borne antigens.

Sedgwick, J. D. et al., *Cell Immunol.* 94: 182–194, 1985 disclose that the repeated exposure of high-IgE-responder rats to an aerosol of an antigen once weekly triggered progressively increasing levels of antigen-specific IgG in the serum. Adoptive transfer of splenocytes from aerosol-exposed animals to naive rats caused a suppression of IgE responses without affecting specific IgG responses.

No method or technique for treating or preventing autoimmune diseases is suggested or disclosed in these references. It is an object of the present invention to provide methods for treating mammals suffering from autoimmune diseases.

Another object of the present invention is to provide pharmaceutical formulations for treating mammals suffering from autoimmune diseases.

A still further object of the invention is to provide a formulation for administration to mammals for the purpose of preventing or treating autoimmune diseases in such mammals.

These and other objects of the present invention will be apparent to those of ordinary skill in the art in light of the present specification, drawings and claims.

BRIEF DESCRIPTION OF THE DRAWINGS

Figure 1:
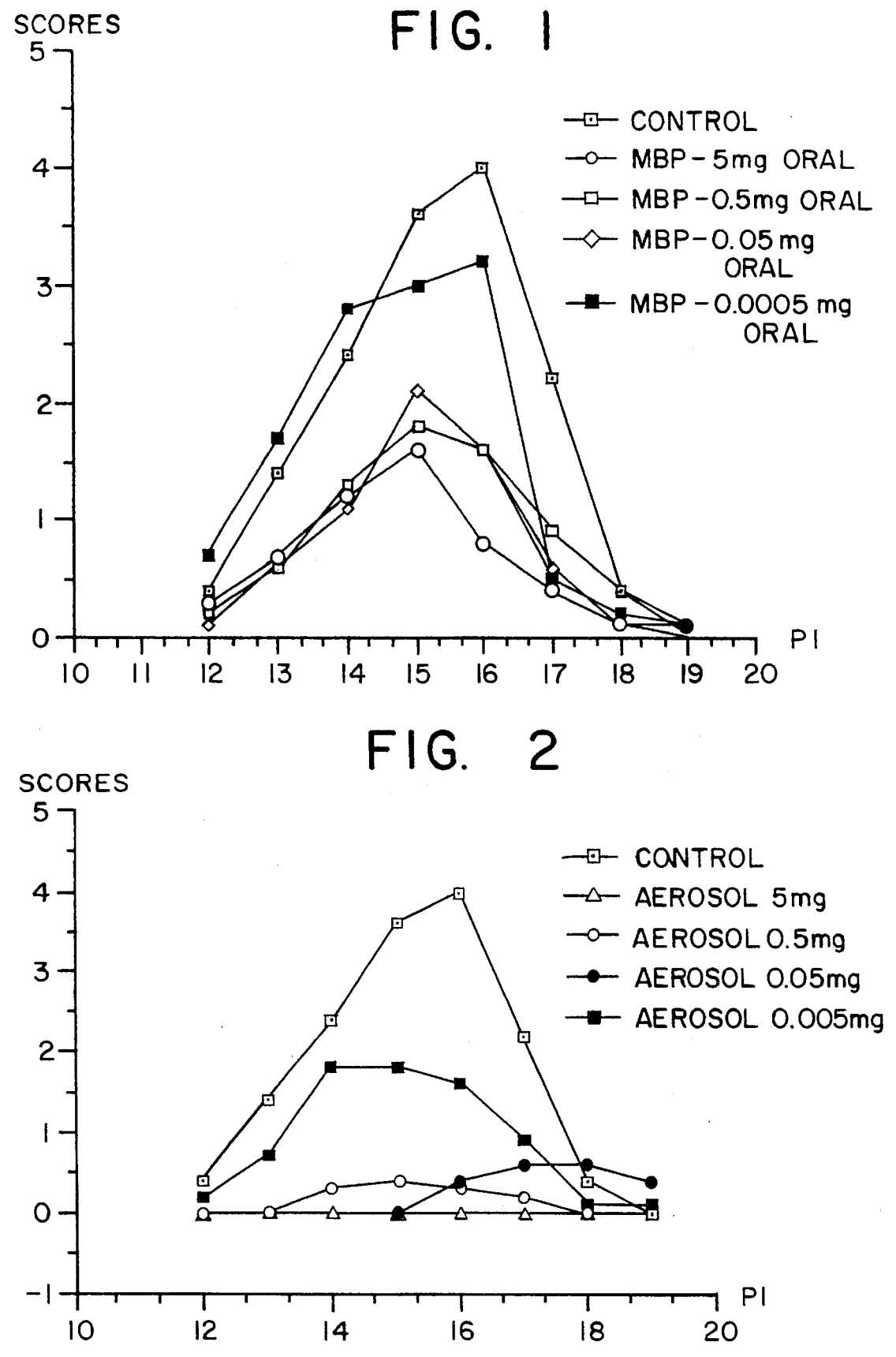

FIG. 1 is a graph showing the disease suppressive effects of various concentrations of orally administered MBP on the course and severity of EAE;

FIG. 2 is a graph showing the disease suppressive effects of various concentrations of MBP administered in aerosol form on the course and severity of EAE;

FIGS. 3(A–D) are a series of graphs directly comparing the effects of various doses of GP-MBP when administered orally or in aerosol form on the course and severity of EAE. FIG. 3A shows the response for a 0.005 mg dose, FIG. 3B shows the response for a 0.05 mg dose.

FIG. 4 is a graph showing the effects of GP-MBP fragments on the course and severity of EAE.

FIG. 5 is a graph showing treatment of animals after induction of EAE.

SUMMARY OF THE INVENTION

Figure 3C:
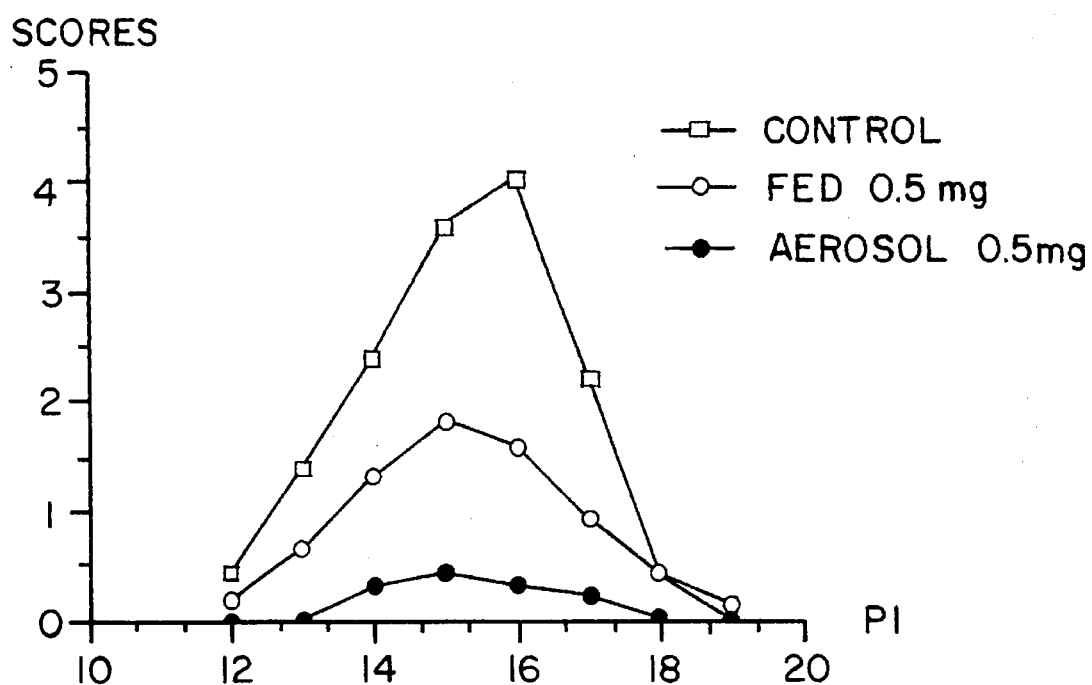
FIG. 3C shows the response for a 0.5 mg dose.
Figure 3D:
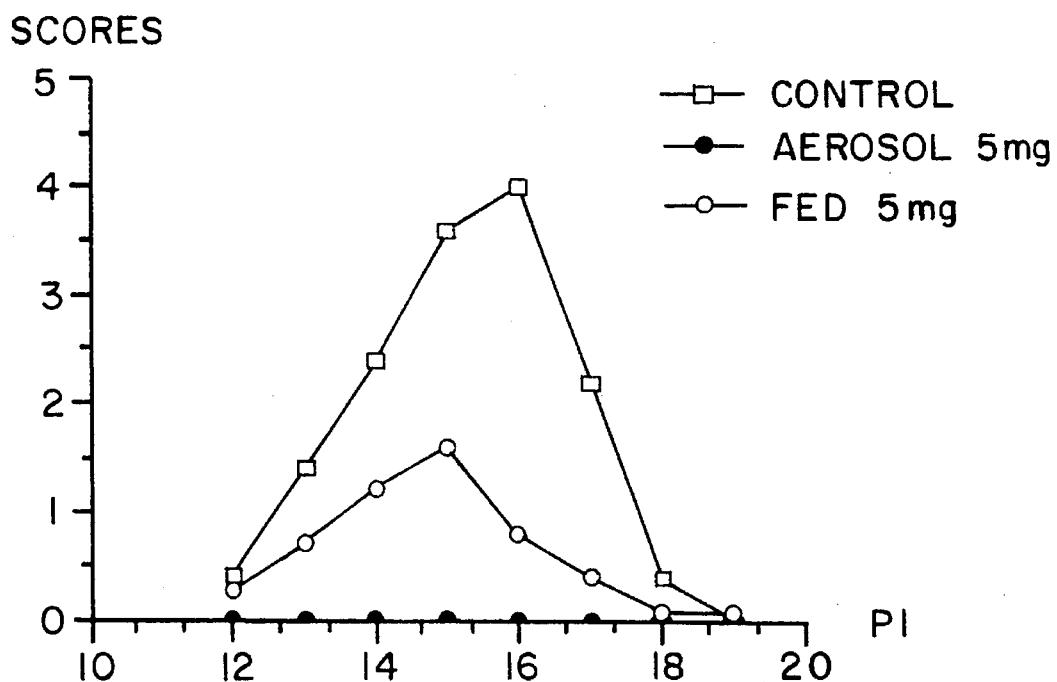
FIG. 3D shows the response for a 5 mg dose.

It has now been discovered that an improved and more effective method for preventing or treating autoimmune diseases in mammals comprises administration in aerosol form of one or more autoantigens specific for the autoimmune disease to be prevented or treated in said mammal.

In one aspect, the present invention provides a method for treating or preventing an autoimmune disease in a mammal by administering to such mammal an effective amount of an aerosol composition comprising at least one autoimmune suppressive agent selected from the group consisting of autoantigens that are specific for such autoimmune disease, autoimmune suppressive fragments and analogs of such autoantigens.

In another aspect, the invention embraces aerosol dosage forms for use in treating autoimmune diseases in mammals. The dosage forms comprise at least one autoimmune suppressive agent selected from the group consisting of autoantigens specific for said autoimmune disease, autoimmune suppressive fragments and analogs of said autoantigens in aerosol form.

DETAILED DESCRIPTION OF THE INVENTION

All patent applications, patents and literature references referred to in this specification are hereby incorporated by reference in their entirety.

It has now been discovered that administration of autoantigens (or autoimmune suppressive fragments or analogs thereof) in aerosol form is effective in treating autoimmune disease in mammals. A particularly surprising and unexpected development is the discovery that administration of autoantigens in aerosol form is more effective in preventing and treating autoimmune diseases in mammals than administration of the same autoantigens in solid form via the oral route. Also surprising is the discovery that it is possible to achieve effective suppression and prevention of autoimmune diseases in mammals using a smaller quantity of such autoantigens in an aerosol form than by administration of a solid dosage form. The aerosol administration of autoantigens has been found to be effective in suppressing both cell-mediated and antibody-mediated autoimmune responses.

Non-limiting examples of autoimmune diseases that may be treated or prevented using the method of the present invention include multiple sclerosis, rheumatoid arthritis, myasthenia gravis, autoimmune thyroiditis, diabetes mellitus (especially Juvenile Onset Diabetes), autoimmune uveoretinitis, systemic lupus erythematosus (SLE or Lupus), adrenalitis and chronic active hepatitis.

As used herein, the term "aerosol" refers to finely divided solid or liquid particles that may be created using a pressurized system such as a nebulizer. The liquid or solid source material contains autoantigens and/or autoimmune disease suppressive fragments and analogs thereof as defined herein.

An autoimmune disease is a malfunction of the immune system of mammals, including humans. In a mammal afflicted with such a disease, the immune system cannot or does not distinguish between exogenous (foreign) substances within the mammal and autologous tissues or substances. As a result, the immune system treats autologous tissues (self antigens) and substances as if they were foreign and evokes the proliferative immune defense that is usually reserved for use against exogenous (foreign) tissues or invading organisms. In essence, one arm of the normal immune system becomes altered and begins a proliferative response against autologous tissues. As employed herein, the term "mammal" refers to all life forms that have an immunoregulatory system and are therefore susceptible to autoimmune diseases.

As employed herein, the term "autoantigen" refers to any substance normally found within a mammal that (1) is not recognized as part of the mammal itself by the lymphocytes or antibodies of that mammal, (2) is attacked by the immunoregulatory system of the mammal as though such antigen were a foreign substance and (3) acts to downregulate the arm of the immune system that is responsible for causing a specific autoimmune disease. The term autoantigen also includes antigenic substances which induce conditions having the symptoms of an autoimmune disease when administered to mammals.

As used herein the term "autoimmune suppressive fragments" includes any peptide or polypeptide containing partial amino acid sequences or moieties of autoantigens and possessing the ability to suppress or prevent an autoimmune response upon aerosol administration. Such fragments need not possess the autoantigenic properties of the entire autoantigen. By way of non-limiting example, when MBP is administered parenterally to mammals in the presence of an adjuvant it induces EAE in susceptible mammals. It has now been discovered that certain non-disease-inducing fragments of MBP (i.e., fragments of MBP which do not induce EAE when administered parenterally with an adjuvant) nevertheless possess autoimmune-suppressive activity when administered orally (or enterally) or in aerosol form to mammals suffering from EAE. Examples of such fragments are reported in U.S. patent application Ser. No. 65,734, and International Patent Application No. PCT/US88/02139, and Examples 2 and 6 below.

As employed herein the term "analogs" of such autoantigens or fragments thereof refers to compounds that are structurally related to these autoantigens or to their autoimmune-suppressive fragments and which possess the same biological activity, i.e. the ability to eliminate or suppress the autoimmune response, upon aerosol administration. By way of non-limiting example, the term includes peptides having amino acid sequences which differ from the amino acid sequence of the autoantigen or disease suppressive fragments thereof by one or more amino acid residues (while still retaining the autoimmune-suppressive activity of the autoantigen or fragment) as well as compounds or compositions which mimic the autoimmune-suppressive activity of the autoantigen in its ability to suppress or alleviate the symptoms of the disease. One example is tissue from an organ that is the target of attack by an arm of the immune system in an autoimmune disease, e.g. the pancreas in diabetes or the white matter of the central nervous system in multiple sclerosis. Another exemplary analog is peptide S79 as disclosed in copending U.S. patent application Ser. No. 65,734 filed Jun. 24, 1987.

As used herein the term "autoimmune-disease suppressive agent" or "autoimmune suppressive agent" refers to a compound or composition which can be administered in an aerosol form to a mammal to suppress, prevent or delay the clinical onset or manifestation of a specific autoimmune disease. The term includes autoantigens that are active against a specific autoimmune disease, as well as autoimmune-suppressive fragments or analogs thereof as defined above.

As employed herein the term "treatment" refers to prophylactic administration to prevent an autoimmune disease in susceptible individuals or to treatment of an active autoimmune disease in an affected individual.

The tolerance induced by the autoimmune-suppressive agents of this invention is dose-dependent; over a broad dosage range of aerosol material it has been found that suppression (or attenuation) of clinical manifestations of the disease (EAE) increases with increasing dosage levels of the aerosolized autoimmune-suppressive agent administered as shown in Examples 2–9 below. Dose dependency was also seen in the arthritis system. Moreover, the aerosol administration of an irrelevant antigen (i.e. one not implicated in an autoimmune disease, such as histone protein, or certain synthetic fragments of MBP) has no effect on the clinical manifestation of the autoimmune disease.

Administration of autoantigens and the aerosol route for the treatment of autoimmune disease has several advantages over other routes of administration. Ease of administration is one important advantage. Also, as shown below in Example 2, aerosol administration of MBP is effective in treating EAE at substantially lower doses than those required to treat this disease when the same agent was administered orally via the oral route in a solid dosage form. A further advantage is that the aerosol administration route involves less exposure of the autoimmugenic agents of the present invention to degradative gastric juices, which may act to reduce the efficacy of such agents.

It should be noted that the amount of autoimmune suppressive agent of the present invention which the treated animal receive via aerosol administration is substantially lower than the total amount of the agent which is administered. It is believed that only 1/200 of the total dosage present in the nebulizer is actually taken up on the pulmonary surface of the treated animals. The majority of the autoimmune suppressive agent nebulized into the cages is not breathed by the animals but non-specifically adheres to the cages and to the animals. Therefore, aerosol administration is much more effective than oral or enteral administration where in the latter case all of the autoimmune suppressive agent is delivered to the treated animals.

Various model systems have been developed for studying autoimmune diseases. Experimental allergic encephalomyelitis (EAE) is an induced T-cell mediated autoimmune disease which has been studied in mice and other mammalian species as a model for Multiple Sclerosis (MS) in several mammalian species. The disease is induced by parenteral administration of MBP and an adjuvant (such as Freund's complete adjuvant). This treatment induces both a monophasic and an exacerbating/remitting form of demyelinating disease (depending on the species and details of administration). The induced disease has the characteristics of MS. Parenteral administration of *Mycobacterium tuberculosis* with Freund's complete adjuvant oil into the dorsal root tail of susceptible mammals induces a disease with the characteristics of human rheumatoid arthritis. In addition, the administration to Lewis rats of S-antigen and an adjuvant induces autoimmune uveoretinitis. Diabetes develops spontaneously in the NOD mouse and the BB rat. Various ones of these model systems have been employed to demonstrate the efficacy and improved treatment provided by the present invention.

The present invention may be used to treat a wide variety of autoimmune diseases, both antibody- and cell-mediated. As shown below in Examples 6 and 7, aerosol administration of an autoantigen (guinea pig MBP) and disease-suppressive fragments thereof caused suppression of both cell (e.g. delayed-type hypersensitivity reactions) and antibody-mediated immune responses. In addition, as shown in the data presented in Example 3, this suppression was actively mediated by spleen cells, implying a role for active cellular suppression in this phenomenon. Therefore, as in the case of immune suppression mediated by the oral administration of autoantigens (disclosed in U.S. patent application Ser. No. 65,734 and the copending International Patent Application PCT/US88/02139), aerosol administration of autoantigens is believed to act, at least in part, by mediating the activity of suppressor T-cells. Non-limiting examples of autoimmune diseases which are cell-mediated include multiple sclerosis, rheumatoid arthritis, autoimmune uveoretinitis, diabetes and autoimmune thyroiditis. Antibody-mediated autoimmune diseases include myasthenia gravis, systemic lupus erythematosus (SLE), pemphigus and thrombic thrombocytopenic purpuria. A non-limiting list of disease models and the specific autoantigens effective in the treatment of these diseases when administered in an aerosol form are set forth below in Table 1.

TABLE 1

| Disease Model | Specific Autoantigen |
| --- | --- |
| Multiple Sclerosis | MBP |
| Rheumatoid Arthritis | Collagen |
| Autoimmune Thyroiditis | Thyroglobulin |
| Myasthenia Gravis | Acetylcholine receptor |
| Autoimmune uveoretinitis | S-antigen |
| Systemic Lupus Erythematosus | DNA |
| Diabetes | Islet cell extract |
| Chronic Active Hepatitis | Liver extract |
| Adrenalitis | Adrenal gland extract |
| Polymyositis | Muscle extract |
| Autoimmune hemolytic anemia | Hematopoietic cells |
| Rheumatic carditis | Heart extract |
| Scleroderma | Skin cell extract |

For any auto immunes disease, tissue extracts can be used as well as the specific antigens described above.

Other autoimmune diseases and their specific autoantigens and/or target tissues are disclosed in Schwartz, R. S. et al. in *Fundamental Immunology, Second Edition,* Paul, W. E., Ed., pg 819–859, Raven Press, N.Y., 1989.

Autoantigens for use in the present invention can be isolated from the tissue which is the target for the particular autoimmune disease. For example, myelin basic protein (MBP) for use in treating MS can be isolated and purified from mammals using the method of Diebler et al. (infra) as shown in Example 1 below.

When treating a disease having the symptoms of rheumatoid arthritis, collagen can be isolated and purified by the method of Trentham et al., *J. Exp. Med.* 146: 857, 1977.

For treating autoimmune uveoretinitis, purified Santigen can be obtained as described in copending application Ser. No. 379,778.

For treating myasthenia gravis, purified acetylcholine receptor can be isolated by the method. of Mcintosh et al. *J. Neuroimmunol.* 25: 75, 1989.

Fragments and analogs of autoantigens for use in the present invention can be synthesized using solid phase synthesis techniques well-known in the art such as those of Merrifield, R. B. (*Fed. Proc. Am. Soc. Ex. Biol.* 21: 412, 1962 and *J. Am. Chem. Soc.* 85: 2149, 1963) and Mitchel, A. R. et al.) as well as Tam, J. et al, (*J. Am. Chem. Soc.* 98: 7357, 1976). Analogs can be constructed by identifying an equivalent amino acid sequence and using the peptide synthesis techniques disclosed above.

Analogs can be provided using the known amino acid sequence of GP-MBP as disclosed in G. Hashim, in *Meylin: Chemistry and Biology* Alan R. Lisa, N.Y., 1980 using techniques described above and in Eyler, E. H., in *Advances in Experimental Medicine and Biology* 98: 259–281, 1978. For example, a peptide having a sequence corresponding to GP-MBP amino acid residues 72–85 as disclosed in Hashim (supra) can be chemically synthesized using the above-described technique with an amino acid substitution at the terminal asparagine position to glutamine. The peptide can be tested for disease-suppressive activity when administered in aerosol form using the techniques as shown in Example 2 below.

Disease-suppressive analogs and fragments can also be obtained using recombinant DNA techniques well-known in the art.

The present invention also provides aerosol pharmaceutical formulations and dosage forms for use in treating mammals suffering from autoimmune diseases. In general such dosage forms contain one or more autoimmune suppressive agents selected from the group consisting of autoantigens directed against the autoimmune disease, disease suppressive fragments and analogs of such autoantigens, in an amount effective to treat or prevent the clinical symptoms of the specific autoimmune disease. Any statistically significant attenuation of one or more symptoms of an autoimmune disease that has been treated pursuant to the method of the present invention is considered to be a treatment of such disease within the scope of the invention.

It will be appreciated that the unit content of active ingredient or ingredients contained in an individual aerosol dose of each dosage form need not in itself constitute an effective amount for treating the particular autoimmune disease since the necessary effective amount can be reached by administration of a plurality of dosage units.

The pharmaceutical formulations of the present invention may include, as optional ingredients, pharmaceutically acceptable carriers, diluents, solubilizing or emulsifying agents, and salts of the type that are well-known in the art. Examples of such substances include normal saline solutions such as physiologically buffered saline solutions and water.

The route of administration of the suppressive agents of the present invention is in an aerosol or inhaled form. The suppressive agents of the present invention can be administered as a dry powder or in an aqueous solution. Preferred aerosol pharmaceutical formulations may comprise for example, a physiologically-acceptable buffered saline solution containing between about 0.15 mg and about 300 mg of one or more of the autoimmune-suppressive agents of the present invention specific for the autoimmune disease to be treated.

Dry aerosol in the form of finely divided solid autoantigen particles that are not dissolved or suspended in a liquid are also useful in the practice of the present invention. Autoantigen may be in the form of dusting powders and comprise finely divided particles having an average particle size of between about 1 and 5 um, preferably between 2 and 3 um. Finely divided autoantigen particles may be prepared by pulverization and screen filtration using technique well known in the art. The particles may be administered by inhaling a predetermined quantity of the finely divided material, which can be in the form of a powder.

Specific non-limiting examples of the carriers and/or diluents that are useful in the pharmaceutical formulations of the present invention include water and physiologically-acceptable buffered saline solutions such as phosphate buffered saline solutions pH 7.0–8.0.

In general, the autoantigen, fragment or analog is introduced to a mammal in an aerosol form in an amount ranging between about 0.1 mg per kg body weight of said mammal and about 15 mg per kg body weight of said mammal per day, and may be administered in a single dosage form or multiple dosage forms. Preferably, the autoantigen, fragment or analog is administered in an amount ranging between 1 mg and about 10 mg per kg body weight of said mammal per day. The exact amount to be administered to a patient will vary depending on the stage and severity of the patient's disease and the physical condition of the patient.

The pharmaceutical formulations of the present invention may be administered in the form of an aerosol spray using for example, a nebulizer such as those described in U.S. Pat. Nos. 4,624,251 issued Nov. 25, 1986; 3,703,173 issued Nov. 21, 1972; 3,561,444 issued Feb. 9, 1971 and 4,635,627 issued Jan. 13, 1971. The aerosol material is inhaled by the subject to be treated. In the present examples (and for purposes of accuracy) the animals treated with aerosol agents were retained in enclosed (airtight) cages, into which the aerosol was dispensed. Thus, the amount of material per unit of area could be determined and the results quantified in terms of unit of aerosol material per unit volume of cage area.

Other systems of aerosol delivery, such as the pressurized metered dose inhaler (MDI) and the dry powder inhaler as disclosed in Newman, S. P. in *Aerosols and the Lung*, Clarke, S. W. and Davia, D. eds. pp. 197–224, Butterworths, London, England, 1984, can be used when practicing the present invention.

Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.).

The working examples presented below illustrate that administration of MBP and Type II collagen in aerosol form was effective in suppressing the clinical symptoms of EAE and collagen-induced arthritis, respectively in a dose-dependent fashion over a wide dosage range. Administration of MBP in aerosol (liquid) form was effective in suppressing EAE when administered before or after disease induction and resulted in both a delay in the onset of disease symptoms and a reduction in the disease severity in treated animals. Both specific antibody and cell-mediated (e.g. delayed-hypersensitivity) reactions were downregulated by aerosol administration of specific autoantigens or disease suppressive fragments thereof. In these instances the specific immunosuppression induced by aerosol administration of autoantigen was mediated by spleen cells and not cells isolated from the thymus of treated animals. These spleen cells were able to actively transfer protection against EAE to naive recipients. Moreover, bovine myelin was also found to be effective in suppressing EAE as was guinea pig MBP, although the latter was more effective disease suppressive agent in rats that had been immunized with GP-MBP to induce EAE. Finally, histological examination of aerosol-treated animals showed that there was an absence of cells actively infiltrating the brains of animals treated according to the present invention. Thus, aerosol administration of an autoantigen to animals suffering from an autoimmune disease was shown to affect clinical symptoms of the disease and prevented cells from migrating into the brain of treated animals. The latter is believed to be a possible mechanism of demyelination causing the symptoms of EAE.

Further details of the invention are set forth below in working examples.

EXAMPLE 1

Autoantigens used in practicing the method of the present invention were obtained using the method and techniques set forth below.

GP-MBP was purified by the method of Diebler, G. E. et al. (*Prep. Biochem.* 2: 139, 1972) from guinea pig brain tissue and was obtained from Pel Freeze (Rogers, Ark.). Briefly, central nervous system tissue was isolated and homogenized in a chloroform-methanol solution, extracted in acetone, filtered and resuspended in the same solution. The solution was extracted in acetone, filtered, resuspended in water, adjusted to pH 3.0 and incubated for 1 hour. The solution was then centrifuged and extracted with 8M urea, CM-5 was added, the pH adjusted to 11, the solution filtered and resuspended twice in urea. The solution was then filtered again, resuspended twice in water, filtered, resuspended in 0.121 N HCl, filtered, dialyzed against 10 volumes of distilled water and lyophilized before use.

Type II collagen used in the Examples presented below was purchased from Genzyme (Boston, Mass.).

EXAMPLE 2

In the experiments described below, Lewis rats, age 6–8 weeks (Charles River, Wilmington, Mass.) in which EAE had been induced on day 0 by footpad injection of 10 micrograms of guinea pig myelin basic protein (GP-MBP) purified as in Example 1 above, in Freund's complete adjuvant as disclosed in *J. Immunol.* 140: 440, 1988. The rats were treated as described below with various doses of GP-MBP in concentrations ranging between 0.005 milligrams and 5 milligrams either orally or in an aerosol spray.

The oral and aerosolized GP-MBP were administered in the same doses on the same days to groups of five rats.

The aerosol GP-MBP was administered in phosphate buffered saline (PBS, pH 7.4) using a nebulizer. Aerosol was administered to test animals through a hole punched in the side of the cage which held the animals. For aerosolization, a nebulizer (American Pharmoseal Co., Valencia, Calif., Catalog No. 002038) was attached to an air pressure outlet delivering the equivalent of 7.4 liters of oxygen (the amount of oxygen used in a hospital for nebulization). The nebulizer produced droplets of spray having a diameter of between about 0.3 micrometers and about 0.5 micrometers in diameter. 25 mg of GP-MBP, purified according to the method of Diebler et al. (supra) was dissolved in 5 ml of PBS. This was then aerosolized over a 10 to 15 minute period to 5 rats per cage (having dimensions 14"×12"×7", for height, width and depth, respectively). During aerosolization, a fine mist was created in the cage and the rats moved about freely. The schedule of treatments was as follows: Treatments (either oral or aerosol) were given on days −10, −7, −5, −3, 0, +2 and +4. Immunization to induce EAE on day 0 resulted in an acute paralytic disease with symptoms manifesting on days 12 to 14 post-immunization. The scoring system was: 0=normal; 1=loss of tail tone; 2=weakness of back legs; 3=paralysis of back legs; 4=front leg weakness; and 5=moribund. EAE severity varied between 2 and 5, depending on the experiment. Animals were scored clinically in a blinded fashion.

Oral GP-MBP was administered as disclosed in copending International Application No. PCT/US88/02139 and U.S. patent application Ser. No. 65,734.

The results are shown in FIGS. 1 and 2.

The graph in FIG. 1 illustrates that the control animals began manifesting disease symptoms at approximately 12 days after induction of EAE. The oral administration of GP-MBP caused a significant decrease in disease symptoms and delayed the onset of disease symptoms in all groups tested with the maximal delaying effects occurring when 0.5 mg or 5 mg of GPMBP was administered orally per animal.

In FIG. 2 it can be seen that the aerosol administration of from 0.005 mg to 5 mg of GP-MBP significantly decreased EAE disease severity in all the animals tested. Administration of 5 mg of GP-MBP totally protected all animals by suppressing all disease symptoms. Aerosol administration was more effective than oral administration, i.e. administration of GP-MBP in aerosol (spray) form reduced disease symptoms at lower effective concentrations (dosage levels) than administration of GPMBP in solid form via the oral route.

A direct comparison of each dose (i.e. 0.005, 0.05, 0.5 and 5 mg/animal), administered either orally or in aerosol form is shown in FIGS. 3A–D. The experiments were performed exactly as above using 5 animals per experimental group. The results confirmed that aerosolization was more effective than oral administration in that smaller quantities of aerosolized GP-MBP were required to suppress EAE disease symptoms This data shows that the route of administration of the material inhaled in the lungs caused the effects shown in FIGS. 1–3 and was not simply due to material that might be swallowed because much larger quantities of orally-administered GP-MBP are required to produce the same effect as when administered in aerosol form.

Different fragments of GP-MBP were tested for their effects on EAE. The MBP fragments were prepared by solid phase peptide synthesis (obtained from Biosearch, San Raphael, Calif.). Fragments corresponding to amino acid residues 16–35, 51–70 and 121–138 of GP-MBP were administered to 5 animals at a concentration of 0.14 mg per animal as described above. None of the above administered fragments were encephalotgenic (i.e. none of the fragments induce EAE upon parenteral administration with an adjuvant). The data is shown in FIG. 4.

In FIG. 4, fragments corresponding to amino acid residues 16–35 and 51–70 of GP-MBP were effective in suppressing the disease symptoms of EAE. A fragment corresponding to amino acid residues 121–138 of GP-MBP had no protective effect on EAE in the treated animals and was similar to controls.

In order to show that aerosolization of GP-MBP was effective in treating EAE when administered after induction of the autoimmune disease, animals were treated with 5 mg GP-MBP per animal either 3 days before induction of EAE or on days +7, 9 and +11 after disease induction. The results are shown in FIG. 5.

The data in FIG. 5 illustrate that aerosol administration of GP-MBP was effective in suppressing whether given 3 days prior to or on days +7, +9, +11 post-induction of EAE.

In order to show the specificity of the autoimmune suppressive treatment, different concentrations of GP-MBP, a fragment of GP-MBP (corresponding to amino acid residues 21–40 of GP-MBP) or histone protein (5 mg/animal, obtained from Sigma Chemical Co., St. Louis, Mo.) were aerosolized to rats in which EAE had been previously induced. The results are shown in FIG. 6.

Figure 6:
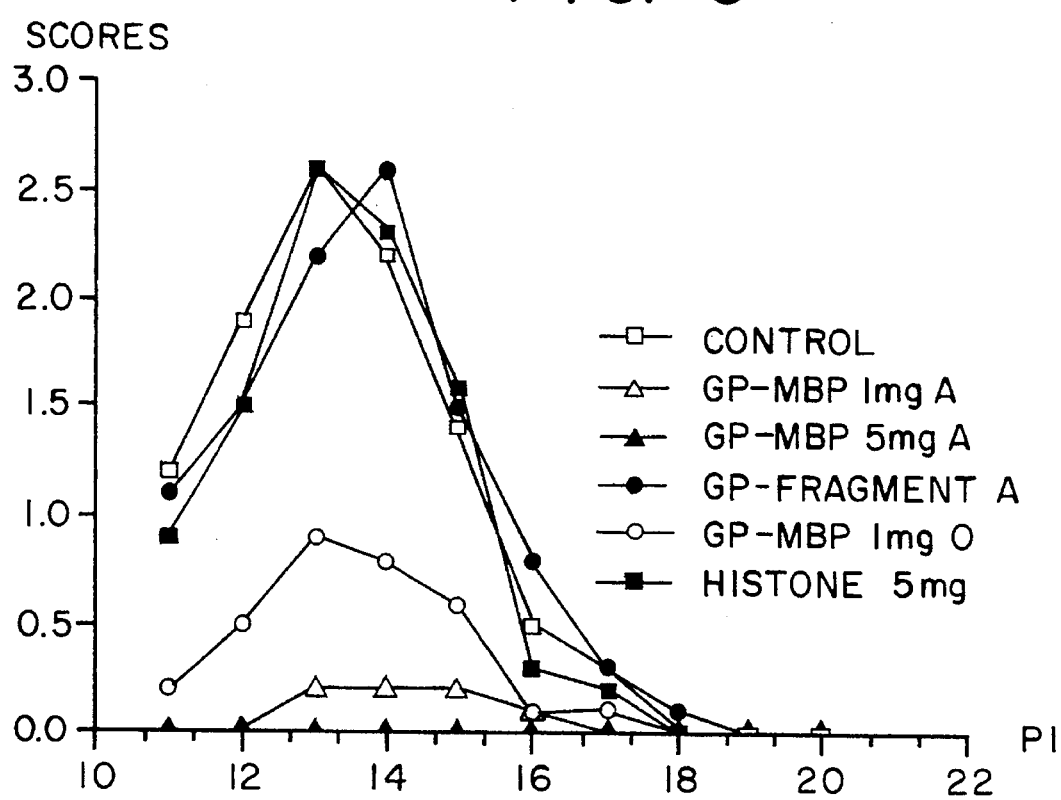
FIG. 6 is a graph showing the effects of various aerosol-administered proteins on EAE.

The data in FIG. 6 show that when 5 mg of GP-MBP was administered in aerosol form, it completely protected the treated animals from induction of EAE. One mg of GP-MBP administered in aerosol form also was protective. Histone protein at 5 mg did not protect against EAE. Histone was used as a control because it is a positively charged protein (as is MBP) and is of a similar molecular weight to MBP, (18,000 daltons as compared to 16,000 daltons for MBP).

In this experiment the GP-MBP fragment administered (21–40) also did not protect. In FIG. 6 it can be seen that 1 mg of GP-MBP given orally protected the animals against EAE but did not protect as well as when the same amount of GP-MBP was given in aerosol form.

EXAMPLE 3

The data presented below represent a series of in vitro experiments which illustrate that spleen cells recovered from animals treated with aerosolized GP-MBP actively suppressed proliferative responses in vitro. Animals received autoantigen in aerosol form on six separate occasions using the identical regimen as in Example 2 above except that they did not receive the −10 day treatment. Modulator cells included thymocytes or splenocytes from treated or non-treated animals. Responder cells included NLB, which is a myelin basic protein specific T-cell line derived from Lewis rats, and NLA is a mycobacterial induced line derived from Lewis rats, the latter used as a negative control. The NLB and NLA cell lines were derived from the popliteal lymph nodes of Lewis rats immunized with either GP-MBP or *Mycobacterium tuberculosis*, respectively in Freund's complete adjuvant using techniques well-known in the art (*J. Immunol.* 131: 2810, 1988). The isolated lymph node cells were restimulated in vitro with antigen plus interleukin-2 (IL-2) before use. The experiments were performed as described in Lider et, el, (*J. Immunol.* 142: 748–752, 1988). The amount of MBP or Concanavalin A (Con A) used in vitro was 10 micrograms/ml and 1.25 micrograms/ml, respectively. Con A was used as a non-specific control. The results are set forth in Tables 2 and 3 below.

TABLE 2

| | SUPPRESSION OF LINE CELLS USING THYMOCYTES FROM TREATED RATS AS MODULATORS | | |
|---|---|---|---|
| RESPONDERS | CONTROL RATS ($\Delta$ CMP × $10^3$) | AEROSOL TREATED RATS ($\Delta$ CMP × $10^3$) | % SUPPRESSION |
| NLB + CON A | 24.648 ± 0.9 | 29.950 ± 6.6 | −17% |
| NLB + GP-MBP | 20.647 ± 6.9 | 22.480 ± 5.6 | −8% |
| NLA + CON A | 19.690 ± 5.9 | 15.941 ± 2.1 | 19% |

TABLE 3

SUPPRESSION OF LINE CELLS USING SPLENOCYTES
FROM CONTROL OR AEROSOL TREATED RATS AS MODULATORS

| RESPONDERS | CONTROL RATS ($\Delta$ CMP × $10^3$) | AEROSOL TREATED RATS ($\Delta$ CMP × $10^3$) | % SUPPRESSION |
|---|---|---|---|
| NLB + CON A | 93.404 ± 1.4 | 87.635 ± 8.1 | 6% |
| NLB + GP-MBP | 63.023 ± 12.9 | 35.523 ± 8.9 | 44% |
| NLA + CON A | 19.892 ± 4.6 | 30.553 ± 3.6 | −53% |

In Tables 2 and 3, it can be seen that when GP-MBP was added to the NLB line in the presence of modulator cells isolated from the spleen of aerosol-treated (with GP-MBP) rats, a 44% suppression of the immune response was observed (Table 3). Therefore, MBP was required to suppress the immune response in aerosol-treated animals and the suppression was antigen specific. When Con A was added to NLB or NLA cells alone, it did not induce suppression.

The data in Table 2 shows that thymocytes were not involved in this immune suppression as neither the control (NLB +Con A) or MBP-treated lines showed evidence of any suppression. Therefore, one of the mechanisms of action of the aerosolization of autoantigens for the treatment of autoimmune diseases appears to be the generation of cells that actively suppress the specific in vitro autoimmune response in treated animals. This was also demonstrated by adoptive transfer of protection by spleen cells from aerosol-treated animal as shown in example 9 below.

EXAMPLE 4

Adjuvant arthritis is a model for rheumatoid arthritis in which arthritis is induced by injecting Freund's complete adjuvant into the base of a rat's tail. Approximately 14 days post-immunization, animals treated in such a fashion develop severe swelling of their joints, characteristic of rheumatoid arthritis in humans.

The effect of aerosol administration of collagen on adjuvant arthritis was studied. The experiments were performed as follows.

Aerosolization of Type II collagen was performed as in Example 2 above for GP-MBP at doses of 0.003, 0.03 and 0.3, milligram per animal. Arthritis was induced by injecting rats in the base of the tail with Freund's complete adjuvant. Five animals were used for each experimental group as described above in Example 2. The animals were treated on days −5, −3, 0, +2 and +4 relative to the induction of arthritis in the aerosol-treated rats.

The mean arthritis score was graded on a scale of 0–4 for each of four paws in the rats as described in *J. Exp. Med.* 146: 857, 1977 as follows: 0-normal, 1-redness only, 2-redness plus mild swelling, 3-severe swelling, 4-joint deformity. The mean arthritis score was calculated on each day for each group of animals. Individual scores for each paw were added together and scores determined for each animal in the group. The mean score was determined by dividing the total score for the group by the number of animals tested.

As an example, the calculation of a mean arthritis score is set forth below.

| Animal Number | Score for Each Paw | Total Score for each animal |
|---|---|---|
| 1 | 1, 1, 1, 1 | 4 |
| 2 | 2, 2, 2, 2 | 8 |
| 3 | 3, 3, 3, 3 | 12 |
| 4 | 4, 4, 4, 4 | 16 |

The mean arthritis score for the four animals in this group would be:

$$\frac{4+8+12+16}{4} = \frac{40}{4} = 10$$

Figure 7:
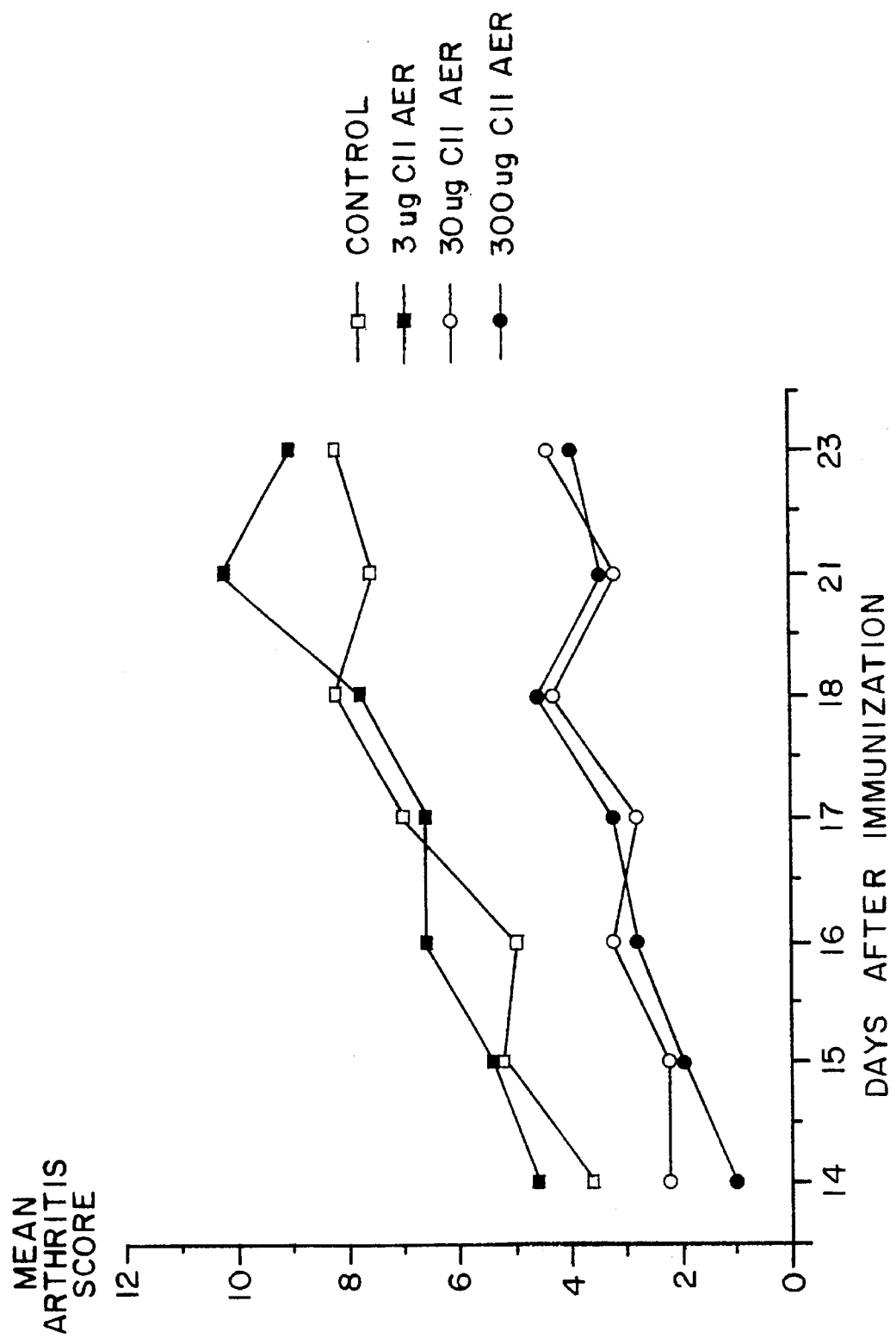
FIG. 7 is a graph showing the effects of aerosolized collagen on the course and severity of collagen-induced arthritis.

The results of the above experiments are shown in FIG. 7 in which the x-axis is the days post-immunization and the y-axis is the mean arthritis score.

As shown in FIG. 7, aerosol administration of collagen at 0.03 and 0.3 but not 0.003 milligrams per rat significantly decreased the mean arthritis score. Therefore, as in the case of aerosol administration of MBP for treating EAE administration of collagen to animals afflicted with adjuvant arthritis was effective in a dose-dependent manner.

EXAMPLE 5

Bovine myelin and bovine MBP were tested for their ability to suppress EAE when administered orally and in aerosol form. Bovine myelin was purchased from Biopure (Boston, Mass.) and consisted of isolated myelin purified on a sucrose gradient according to routine procedures well-known in the art. EAE was induced and Bovine myelin and MBP were administered in oral or aerosol form as in Example 2 above. The results are set forth in Table 4 below.

TABLE 4

| GROUP | Days PI | | | | | | | | |
|---|---|---|---|---|---|---|---|---|---|
| | 12 | 13 | 14 | 15 | 16 | 17 | 18 | 19 | 20 |
| Control | 0.9[1] | 1.7 | 2.3 | 2.4 | 1.9 | 1.5 | 0.9 | 0.7 | 0.2 |
| Bovine myelin, 1000 mg | 0 | 0 | 0.3 | 0.4 | 0.3 | 0.2 | 0 | 0 | 0 |
| Bovine myelin, 100 mg | 0.3 | 0.4 | 0.6 | 0.8 | 0.5 | 0.5 | 0.1 | 0 | 0 |
| Bovine myelin, MBP, 10 mg | 0.2 | 0.2 | 0.5 | 0.7 | 0.4 | 0.4 | 0.3 | 0 | 0 |
| Bovine myelin, 10 mg (A) | 0 | 0 | 0 | 0.4 | 0.7 | 0.5 | 0.7 | 0.2 | 0 |
| Bovine myelin, 1 mg | 0.8 | 0.7 | 0.8 | 1.3 | 1.1 | 0.7 | 0.4 | 0.2 | 0 |
| Bovine myelin, 0.1 mg | 0.7 | 1.1 | 1.3 | 1.2 | 1.3 | 0.9 | 0.4 | 0.3 | 0.1 |

TABLE 4-continued

| GROUP | Days PI | | | | | | | | |
|---|---|---|---|---|---|---|---|---|---|
| | 12 | 13 | 14 | 15 | 16 | 17 | 18 | 19 | 20 |
| Bovine-MBP, 1 mg | 0.2 | 0.4 | 0.7 | 0.6 | 0.4 | 0.2 | 0 | 0 | 0 |
| GP-MBP, 1 mg | 0 | 0 | 0 | 0.1 | 0.3 | 0.4 | 0.1 | 0 | 0 |

[1]Mean paralytic score
A = aerosol
PI = post-immunization days

Referring to Table 4 above, Bovine myelin was effective in treating EAE when administered in oral and aerosol form. Ten mg of Bovine myelin administered in aerosol form was as effective in suppressing autoimmune disease symptoms as 1000 mg of the same material administered orally in liquid form. In addition, oral administration of Bovine MBP was also effective in suppressing EAE symptoms induced by GP-MBP.

EXAMPLE 6

Delay-type hypersensitivity (DTH) responses were measured in Lewis rats in which EAE had been induced and treated with either oral or aerosol-administered GP-MBP. Delay-type hypersensitivity (DTH) is a classic measure of in vivo cell mediated immunity.

Rats (5 per group) were treated with 5 mg of GP-MBP administered either orally or in aerosol form and DTH responses were measured as above. Delay-type hypersensitivity was induced by injecting 10 micrograms of GP-MBP into the pinna of a rat's ear and the subsequent swelling measured 48 hours later according to methods described in *J. Immunol.* 125: 283, 1980.

DTH responses in rats in which EAE had been induced as in Example 2 above were measured as above after various treatments. Rats (5 per group) were treated with 5 mg/animal of various MBP preparations in aerosol form and DTH responses measured. The results are set forth below in Table 5.

TABLE 5

| | DTH Response (× $10^{-2}$ Inches) | | |
|---|---|---|---|
| Treatment | Control | Treated | Significance[1] |
| GP-MBP, −3 | 1.150 | 0.180 | 0.000 |
| GP-MBP, +7, +9, +11 | 1.150 | 0.580 | 0.004 |
| GP-myelin | 1.150 | 0.040 | 0.000 |
| GP-MBP fragment (16–35) | 1.150 | 0.850 | 0.036 |
| GP-MBP fragment (51–70) | 1.150 | 1.000 | 0.251[2] |
| GP-MBP fragment (121–138) | 1.150 | 0.911 | 0.096[2] |
| Bovine MBP | 1.150 | 0.330 | 0.000 |
| Rat MBP | 1.150 | 1.080 | 0.585[2] |

[1]Determined by student's t-test
[2]Not significant by student's t-test

Referring to the data in Table 5, aerosol administration of GP-MBP 3 days before (−3) or on days 7, 9, and 11 postinduction (+7, +9, +11) of EAE significantly suppressed DTH responses in aerosol-treated rats. Aerosol treatment using whole guinea pig myelin, administered on days −10, −7, −5, −3, 0, +2 and +4 was also effective in suppressing DTH responses in treated animals.

Certain fragments of GP-MBP (administration as above) were also effective in suppressing DTH responses in aerosol-treated animals. A GP-MBP fragment, corresponding to GP-MBP amino acid residues 16–35, suppressed DTH responses when administered in aerosol form (Table 5); a fragment corresponding to GP-MBP amino acid residues 51–70 was ineffective in suppressing DTH responses and a fragment corresponding to GPMBP amino acid residues 121–138 induced a low level of suppression of DTH responses. This data shows that certain fragments of GP-MBP were effective in suppressing DTH responses.

Finally, aerosolized Bovine MBP was effective in suppressing DTH responses in animals immunized with GP-MBP whereas aerosolized rat MBP was ineffective in this respect. These data also show that aerosolization of a protein itself is not responsible for the immunne suppression of DTH and only specific proteins produced this effect.

EXAMPLE 7

The effects of aerosol administration of GP-MBP on antibody production in rats in which EAE had been induced was examined.

Antibody responses were measured in animals treated with aerosolized GP-MBP and a variety of control antigens including histone and bovine serum albumin (BSA). In these experiments, serum was taken and antibody titers were measured in 5 animals per group treated on days −10, −7, −5, −3, 0, +2 and +4 relative to immunization with GP-MBP in Freund's complete adjuvant three weeks after immunization in the treated rats. Antibody titers were measured by ELISA (as described in Lider, et, al *J. Immunol* 142: 748–752 1989). The results are set forth in Table 6 below.

TABLE 6

| | SERUM ANTIBODY LEVELS | | | |
|---|---|---|---|---|
| Group | 1/10,000 | 1/20,000 | 1/40,000 | 1/80,000 |
| Control | 0.520 | 0.239 | 0.382 | 0.143 |
| GP-MBP 5 mg (A) | 0.276 | 0.121 | 0.089 | 0.074 |
| GP-MBP, 1 mg (A) | 0.579 | 0.380 | 0.349 | 0.250 |
| GP-MBP, 1 mg (O) | 0.437 | 0.275 | 0.203 | 0.157 |
| Histone, 5 mg | 1.405 | 1.229 | 0.782 | 0.644 |
| BSA, 5 mg | 0.405 | 0.489 | 0.382 | 0.315 |
| PBS | 0.913 | 0.953 | 0.769 | 0.624 |
| BP-MBP-fragment (21–40, 0.174 mg/rat) | 0.226 | 0.243 | 0.192 | 0.132 |

The results presented above show that in animals treated with 5 mg of aerosolized GP-MBP there was a statistically significant decrease in antibody levels as compared to controls. Neither PBS, bovine serum albumin (BSA, Boehring-Mannheim) nor histone (Sigma Chemical Co., St. Louis, Md.) suppressed antibody responses. In addition, a GP-MBP fragment corresponding to GP-MBP amino acid residues 21–40 also suppressed specific MBP antibody responses in a statistically significant manner when administered in aerosol form. The results presented above show a decrease in antibody response to MBP in animals treated with 5 mg aerosolized MBP.

EXAMPLE 8

EAE was induced in rats and the animals were treated with GP-MBP by aerosol as described above in Example 2 (25 mg of GP-MBP in 5 ml of PBS administered to five rats per group on days −10, −7, −5, −3, 0, +2 and +4). Control animals were treated with PBS alone. Rats were sacrificed 16 days after immunization, their brains fixed in formaldehyde, slides of paraffin-embedded tissue prepared for individual rats and the number of parenchymal inflammatory foci in the rat's brains were counted in a blinded fashion. Histologic analysis was performed on the rats as described (Higgins et al., *J. Immunol.* 140: 440, 1988). The results of this biological analysis is set forth below.

In these studies, there was an absence of cells infiltrating brain parenchyma in MBP-treated animals. The results were as follows:
controls (n=6) # foci=48,25,14,11,8,4; average foci/animal= 18.3
aerosol treated (n=4) # foci=2,0,0,0; average foci/animal= 0.5

This demonstrated that aerosol treatment not only affected clinical disease and immunologic function, but also prevented movement of cells into the brain. Movement of cells into the brain is the primary mechanism underlying the disease process in EAE.

EXAMPLE 9

A major question related to the protection of animals from EAE following aerosolization of GP-MBP is the mechanism of action of the specific immune suppression. The experiments described below show that active cellular mechanisms are triggered by aerosol administration of MBP. In these experiments cells that adoptively transfer protection against EAE to naive animals were recovered from the spleens of aerosol-treated animals.

Lewis rats were treated as described above in Example 2 using 5 rats per group (5 mg per rat of GP-MBP in PBS administered 7 times). Three days following the last treatment, spleen cells were removed from treated animals, single cell suspensions prepared, injected intraperitoneally into 5 naive animals ($9 \times 10^8$ cells per each recipient) that were then immunized with MBP in Freund's complete adjuvant. The results are shown in FIG. 8.

Figure 8:
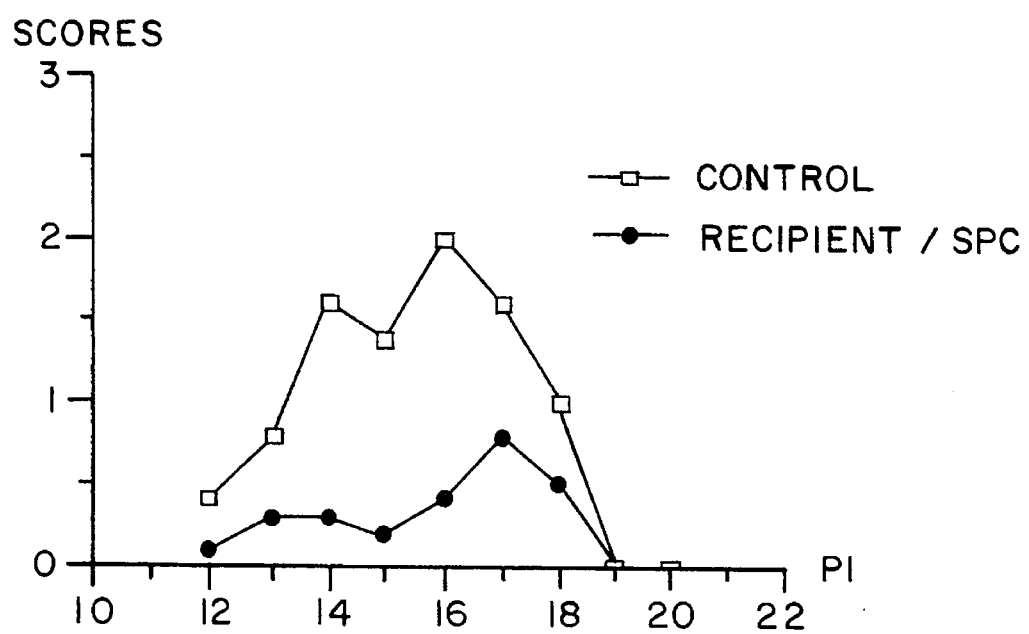
FIG. 8 is a graph showing the transfer of immunity against EAE to recipient animals mediated by spleen cells isolated from animals treated according to the method of the present invention.

As shown in FIG. 8, there was a marked diminution of disease severity in rats which received spleen cells from MBP-treated animals. In addition, DTH responses were measured in recipient animals and there was marked inhibition of DTH responses to MBP in aerosol-treated rats (data not shown).

Therefore, spleen cells from aerosol-treated animals were capable of adoptively transferring protection to the naive recipients against EAE and also downregulated DTH responses in these animals.

What is claimed is:

1. A method for treating a cell-mediated autoimmune disease in a mammal by suppressing an autoimmune response associated with said disease, which comprises administering to said mammal through nasal administration an effective amount for suppressing said autoimmune response of at least one agent selected from the group consisting of:
   (a) MBP or an autoimmune response suppressive fragment of MBP when said autoimmune disease is multiple sclerosis: and
   (b) collagen or an autoimmune response suppressive fragment of collagen when said autoimmune disease is rheumatoid arthritis.

2. The method of claim 1 wherein said agent is MBP.

3. The method of claim 1 wherein said autoimmune disease is multiple sclerosis.

4. The method of claim 1 wherein said agent is collagen.

5. The method of claim 1 wherein said autoimmune disease comprises rheumatoid arthritis.

6. A method for treating or preventing the autoimmune disease multiple sclerosis in a mammal afflicted with said disease by suppressing an autoimmune response associated with said disease, which comprises nasally administering to said mammal an effective amount to suppress said autoimmune response of at least one agent selected from the group consisting of MBP, and an autoimmune disease suppressive fragment of MBP.

7. The method of claim 6 wherein said autoantigen is MBP.

8. A method for treating or preventing autoimmune arthritis in a mammal afflicted with said disease by suppressing an autoimmune response associated with said disease, which comprises administering through nasal administration to said mammal of an effective amount to suppress said autoimmune response of at least one agent selected from the group consisting of collagen, and an autoimmune disease suppressive fragment of collagen.

9. The method of claim 8 wherein said agent is collagen.

10. The method of claim 1 comprising nasal administration of a powder.

11. The method of claim 1 wherein said agent is type II collagen.

12. The method of claim 1 wherein said agent is administered in tissue that is the target of autoimmune attack.

13. The method of claim 6 wherein said MBP is administered in tissue that is the target of attack in said multiple sclerosis.

14. The method of claim 8 wherein said collagen comprises type II collagen.

* * * * *

UNITED STATES PATENT AND TRADEMARK OFFICE
CERTIFICATE OF CORRECTION

PATENT NO. : 5,571,499
DATED : November 5, 1996
INVENTOR(S) : David A. Halfer et al.

It is certified that error appears in the above-indentified patent and that said Letters Patent is hereby corrected as shown below:

IN THE TITLE PAGE:

[63] after "Ser. No. 2,139", please insert -- ,Jun. 24, 1988 --.

Signed and Sealed this

Seventeenth Day of June, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,571,499
DATED : November 5, 1996
INVENTOR(S) : Hafler, et. al.

It is certified that error appears in the above-identified patent and that said Letters Patent is hereby corrected as shown below:

Title page, item [54] and col. 1, line 2, after "BY", delete "AEROSOL" and insert -- NASAL --.

Col. 1, line 15, after "1987", insert --, now abandoned--.
Col. 7, line 46, after "S" insert -- - --.
Col. 11, line 5, after "GP" insert -- - --.
Col. 11, line 14, after "GP" insert -- - --.
Col. 11, line 50, before "9" insert -- +--.
Col. 16, line 5, after "GP" insert -- - --.

Signed and Sealed this

Fifteenth Day of December, 1998

*Attest:*

BRUCE LEHMAN

*Attesting Officer*  *Commissioner of Patents and Trademarks*